(12) United States Patent
Hacker et al.

(10) Patent No.: US 7,074,743 B1
(45) Date of Patent: Jul. 11, 2006

(54) HERBICIDAL COMPOSITION COMPRISING 4-IODO-2-[3-(4-METHOXY-6-METHYL-1,3,5-TRIAZIN-2-YL)UREIDOSULFONYL]BENZOIC ESTERS

(75) Inventors: Erwin Hacker, Hochheim (DE); Martin Hess, Mainz-Bretzenheim (DE); Heinz Kehne, Hofheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/361,461

(22) Filed: Jul. 27, 1999

Related U.S. Application Data

(63) Continuation-in-part of application No. 08/659,721, filed on Jun. 6, 1996, now Pat. No. 5,990,047.

(30) Foreign Application Priority Data

Jun. 8, 1995 (DE) ................................ 195 20 839

(51) Int. Cl.
A01N 43/88 (2006.01)
A01N 43/66 (2006.01)
A01N 43/50 (2006.01)
A01N 37/34 (2006.01)
A01N 39/02 (2006.01)

(52) U.S. Cl. ...................... 504/132; 504/131; 504/133; 504/134; 504/135; 504/139; 504/141; 504/145; 504/146

(58) Field of Classification Search ........ 504/129–149, 504/118
See application file for complete search history.

(56) References Cited

U.S. PATENT DOCUMENTS

| | | | |
|---|---|---|---|
| 5,463,081 A * | 10/1995 | Ort et al. ................... 549/13 |
| 5,872,077 A | 2/1999 | Hacker et al. ............. 504/134 |
| 6,486,096 B1 * | 11/2002 | Hacker et al. ............. 504/133 |
| 6,492,301 B1 * | 12/2002 | Hacker et al. ............. 504/128 |
| 6,750,177 B1 * | 6/2004 | Hacker et al. ............. 504/128 |
| 2003/0176284 A1 * | 9/2003 | Hacker et al. ............. 504/134 |
| 2003/0181333 A1 * | 9/2003 | Hacker et al. ............. 504/133 |
| 2003/0186816 A1 * | 10/2003 | Hacker et al. ............. 504/134 |

FOREIGN PATENT DOCUMENTS

WO 90/02120 * 3/1990

* cited by examiner

Primary Examiner—John Pak
(74) Attorney, Agent, or Firm—Frommer Lawrence & Haug LLP

(57) ABSTRACT

Herbicidal compositions comprising
A) at least one compound from the group of the substituted phenylsulfonylureas of the formula I and their agriculturally acceptable salts

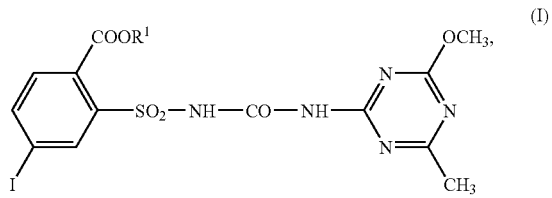

(I)

in which
$R^1$ is $(C_1-C_8)$alkyl, $(C_3-C_4)$alkenyl, $(C_3-C_4)$alkynyl or $(C_1-C_4)$alkyl which is mono- to tetrasubstituted by radicals selected from the group consisting of halogen and $(C_1-C_2)$alkoxy, and
B) at least one herbicidally active compound from the group of compounds composed of
Ba) herbicides which act selectively against grasses in cereals and/or maize,
Bb) herbicides which act selectively against dicots in cereals and/or maize,
Bc) herbicides which act selectively against grasses and dicots in cereals and/or maize and
Bd) herbicides which act non-selectively against grass weeds and broad-leaved weeds in non-crop areas and/or selectively against grass weeds and broad-leaved weeds in transgenic crops.

14 Claims, No Drawings

HERBICIDAL COMPOSITION COMPRISING 4-IODO-2-[3-(4-METHOXY-6-METHYL-1,3,5-TRIAZIN-2-YL)UREIDOSULFONYL]BENZOIC ESTERS

This application is a continuation-in-part of application U.S. Ser. No. 08/659,721, filed Jun. 6, 1996, now U.S. Pat. No. 5,990,047, which claims priority to German application No. 195 20 839.0, filed Jun. 8, 1995, both incorporated herein by reference The invention lies in the technical field of the crop protection products, in particular the invention relates to herbicidal compositions comprising 4-iodo-2-[3-(4-methoxy-6-methyl-1,3,5-triazin-2-yl)ureido-sulfonyl]benzoic esters and/or their salts.

WO 92/13845 (PCT/EP92/00304) discloses iodinated arylsulfonylureas of the formula 1 and their salts

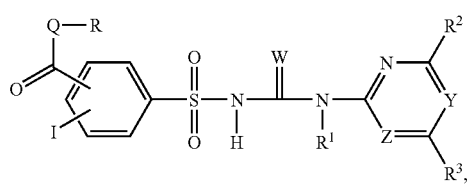

(1)

the formula 1 embracing a large number of possible individual compounds due to the extensive and broad definition of the radicals Q, W, Y, Z, R, $R^1$, $R^2$ and $R^3$.

In the chemical Example 9 of WO 92/13845, methyl 2-[[[(4,6-dimethoxy-2-pyrimidinyl)amino]carbonyl]amino]sulfonyl]-4-iodobenzoate is synthesized, while the chemical Example 10 relates to the preparation of ethyl 2-iodo-3-[[[[4-methoxy-6-methyl-1,3,5-triazin-2-yl)amino]carbonyl]amino]sulfonyl]benzoate. A chemical example of the synthesis of 4-iodo-2-[3-(4-methoxy-6-methyl-1,3,5-triazin-2-yl)ureidosulfonyl]benzoic esters is not described.

Table 3 of WO 92/13845 lists compounds of the formula 2

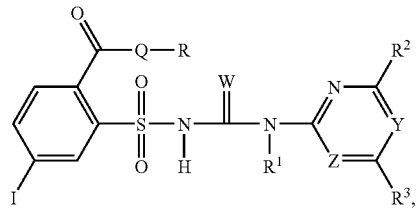

(2)

the Examples No. 7, 44, 81, 118, 155, 192, 229, 237, 245, 253, 261, 269, 277, 298, 299 and 300 relating to those compounds of the formula 2 in which Y and Z are nitrogen, Q and W are oxygen, $R^1$ is hydrogen, $R^2$ is $OCH_3$ and $R^3$ is $CH_3$. However, a melting point is only given in Examples 7 (R=methyl) and 44 (R=ethyl) and in Examples 298 to 300 (sodium, lithium, potassium salt; R is in each case methyl).

No biological examples of the compounds listed above individually are mentioned in WO 92/13845. Rather, a general mention is made of the possibility of using the compounds of the formula 1 with other herbicides. This is followed by an exemplary enumeration of more than approximately 250 various standard substances, and amongst those mentioned individually are acifluorfen, alachlor, amidosulfuron, atrazine, bentazone, bifenox, bromoxynil, chlortoluron, chlorsulfuron, dicamba, diclofop-methyl, difenzoquat, diflufenican, fenoxapropethyl, flamprop-methyl, fluoroglycofen-ethyl, fluroxypyr, fomesafen, glufosinate, glyphosate, imazamethabenzmethyl, ioxynil, isoproturon, lactofen, MCPA, mecoprop, methabenzthiazuron, metolachlor, metribuzin, metsulfuronmethyl, pendimethalin, primisulfuron-methyl, terbuthylazine, thifensulfuron-methyl, tralkoxydim, triasulfuron and tribenuronmethyl. Neither information with a view to the purposes of a joint application which exceed a mere mention of the substances nor, for example, a motivation for the specific choice and combination of certain active substances can be found in WO 92/13845.

While most of the iodinated arylsulfonylureas disclosed in WO 92/13845 as set forth in formula 1 have a useful to good activity against a broad spectrum of economically important mono- and dicotyledon harmful plants and while even weeds which occur under the specific conditions of rice growing such as, for example, *Sagittaria, Alisma, Eleocharis, Scirpus, Cyperus* etc., are controlled with the aid of active substances of the formula 1, the individual active substances are frequently insufficient for controlling the spectrum of mono- and dicotyledon weeds which occurs under realistic agricultural conditions, especially in cereals or maize, but also in other crops.

In the light of the prior art given and discussed herein, it was therefore an object of the invention to provide novel herbicidally active mixtures which allow the grower to control the weed spectrum, or individual weed species which are difficult to combat, in cereals, maize and other crop species by means of one application, or a few applications, of herbicides. Moreover, the mixtures of herbicidally active substances which are known in principle should contribute to closing so-called "activity gaps" and simultaneously to reduce the rates of the individual active substances as far as this is possible.

These and other objects which have not been mentioned individually are achieved by herbicidal compositions which are characterized in claim 1. Thus, the invention relates to herbicidal compositions comprising A) at least one herbicidally active substance from the group of the substituted phenylsulfonylureas of the formula I and their agriculturally acceptable salts

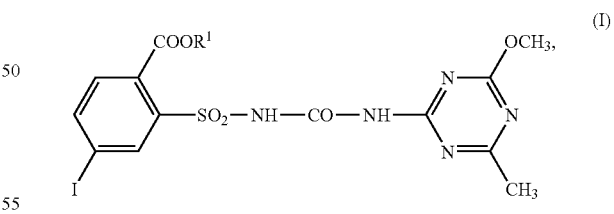

(I)

in which $R^1$ is $(C_1–C_8)$alkyl, $(C_3–C_4)$alkenyl, $(C_3–C_4)$alkynyl or $(C_1–C_4)$alkyl which is mono- to tetrasubstituted by radicals selected from the group consisting of halogen and $(C_1–C_2)$alkoxy, and B) at least one herbicidally active compound from the group of compounds composed of Ba) herbicides which act selectively against grasses in cereals and/or maize, Bb) herbicides which act selectively against dicots in cereals and/or maize, Bc) herbicides which act selectively against grasses and dicots in cereals and/or maize and Bd) herbicides which act non-selectively against grass weeds and broad-leaved weeds in non-crop areas and/or selectively against grass weeds and broad-leaved weeds in transgenic crops.

The combinations according to the invention of herbicidally active substances of types A and B allow a particularly advantageous control, as required by the grower, of the weed spectrum including even individual species which are difficult to combat. Moreover, the combinations according to the invention allow the rates of the amounts of active substance of the individual components of the combination to be reduced, which makes possible a more economical solution from the point of view of the user. Finally, it was surprising that increased activities were achieved which exceed the level to be expected, the herbicidal compositions of the invention thus exhibiting a wide range of synergistic activities.

While the phenylsulfonylureas of the formula I which have an iodine substitution in the 4-position of the phenyl ring are encompassed in principle for example by the formula 1 in WO 92/13845, the prior art does not show their outstanding suitability as components in synergistic mixtures with other herbicides. In particular, the prior-art literature mentions nothing about such an exceptional position of the strictly limited and clearly defined group of the 4-iodo-2-[3-(4-methoxy-6-methyl-1,3,5-triazin-2-yl)ureido-sulfonyl]benzoic esters which are optionally present in the form of their salts.

Particularly interesting as type A components for the combinations of the invention are compounds of the formula I or their salts in which $R^1$ is methyl, ethyl, nor isopropyl, n-, tert-, 2-butyl or isobutyl, n-pentyl, isopentyl, n-hexyl, isohexyl, 1,3-dimethylbutyl, n-heptyl, 1-methylhexyl or 1,4-dimethylpentyl.

In a particularly preferred embodiment, herbicidal compositions according to the invention comprise a type A compound of the formula I or a salt thereof in which $R_1$ is methyl.

The type A compounds (formula 1) can form salts in which the hydrogen of the —SO$_2$—NH— group is replaced by an agriculturally suitable cation. Examples of these salts are metal salts, in particular alkali metal salts (for example sodium or potassium salts) or alkaline earth salts, or else ammonium salts or salts with organic amines. Equally, salt formation can be effected by an addition reaction of a strong acid with the heterocyclic moiety of the compounds of the formula I. Examples which are suitable for this purpose are HCl, ENO$_3$ trichloroacetic acid, acetic acid or palmitic acid.

Particularly advantageous type A compounds are those in which the salt of the herbicide of formula (I) is formed by replacing the hydrogen of the —SO$_2$—NH— group by a cation from the group of the alkali metals, alkaline earth metals and ammonium, preferably sodium.

If the compounds of the formula I contain one or more asymmetric carbon atoms or else double bonds which are not specifically mentioned in the formula, they are still type A compounds. The formula I embraces all stereoisomers which are possible and which are defined by their specific spatial form, such as enantiomers, diastereoisomers and Z- and E-isomers, and these can be obtained from the stereoisomer mixtures by customary methods or prepared by stereoselective reactions in combination with the use of stereochemically pure starting materials. Thus, the above-mentioned stereoisomers can be employed according to the invention in pure form and in the form of their mixtures.

As a rule, the type B components are standard herbicides which have, however, been selected with certain criteria in mind. Thus, with two exceptions (subgroup Bd), they are herbicides which act selectively in cereals and/or in maize against undesirable plants. The harmful plants to be controlled include mainly grasses and/or dicots. With a view to the activity of the type B standard herbicides, in turn, the substances can be ranked according to the controlled plants on which they focus. Thus, some of the type B herbicides act almost exclusively against grasses and others mainly against dicots, while the type B herbicides from subgroup Bc) are employed both against grasses and against dicots. In any case, however, the combinations according to the invention result in an optimized spectrum of action by complementing and intensifying the herbicidal properties of the type A compounds. Last but not least, this also applies to the type B compounds from group Bd), which embraces the herbicides which are active against grass weeds and dicotylden weeds and are non-selective in non-crop areas and/or selective in transgenic crops.

In a preferred variant, a composition according to the invention is characterized in that it comprises, as type B herbicides, one or more herbicides which act selectively against grasses in cereals and/or in maize and which are from the group embracing the 2-(4-aryloxyphenoxy)propionic acids and their esters, ureas, sulfonylureas, cyclohexanedione oximes, arylalanines, 2,6-dinitroanilines, imidazolinones and difenzoquat. Besides the abovementioned individual substances, said classes of chemicals include a series of grass herbicides, which are suitable as components in combinations with type A compounds.

Preferred compositions according to the invention comprise, as type B herbicides, one or more herbicides which act selectively against grasses in cereals and which are from the group consisting of B1) fenoxaprop, fenoxaprop-P

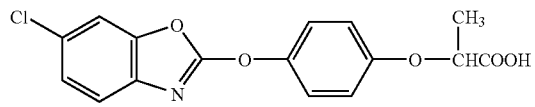

(±)-2-[4-(6-chloro-1,3-benzoxazol-2-yloxy)phenoxy]-propionic acid, which embraces, inter alia, the use form fenoxapropethyl, ethyl,

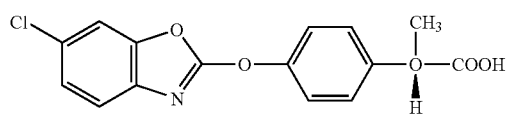

(R)-2-[4-(6-chloro-1,3-benzoxazol-2-yloxy)phenoxy] propionic acid, which embraces, inter alia, the most frequent use form fenoxaprop-P-ethyl, the abovementioned compounds B1) being known from Pesticide Manual, 10th Edition 1994, pp. 439–441 and 441–442, B2) isoproturon

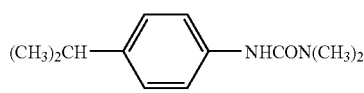

3-(4-isopropylphenyl)-1,1-dimethylurea, Pesticide Manual, 10th Edition 1994, pp. 611–612, B3) diclofop

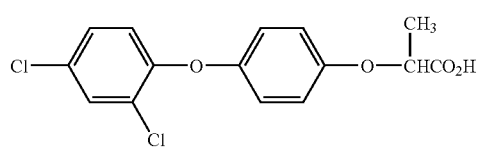

(RS)-2-[4-(2,4-dichlorophenoxy)phenoxy]propionic acid, which embraces, inter alia, the methyl ester, i.e. diclofop-methyl, as the most important use form,
Pesticide Manual, 10th Edition 1994, pp. 315–317;

B4) clodinafop,

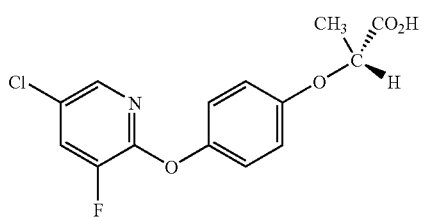

(R)-2-[4-(5-chloro-3-fluoro-2-pyridyloxy)phenoxy]propionic acid,
which embraces, in particular, also the use form clodinafop-propargyl,
Pesticide Manual, 10th Edition 1994, pp. 216–217, B5) mixtures of B4) and
cloquintocet,

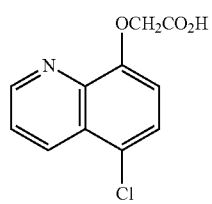

(5-chloroquinolin-8-yloxy) acetic acid,
which is also employed as cloquintocet-mexyl and is a particularly preferred safener for B4), Pesticide Manual, 10th Edition 1994, pp. 226–227, B6) chlortoluron

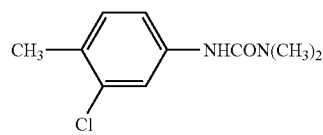

3-(3-chloro-p-tolyl)-1,1-dimethylurea
Pesticide Manual, 10th Edition 1994, pp. 195–196, B7) methabenzthiazuron

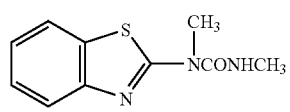

1-(1,3-benzothiazol-2-yl)-1,3-dimethylurea Pesticide Manual, 10th Edition 1994, pp. 670–671, B8) imazamethabenz

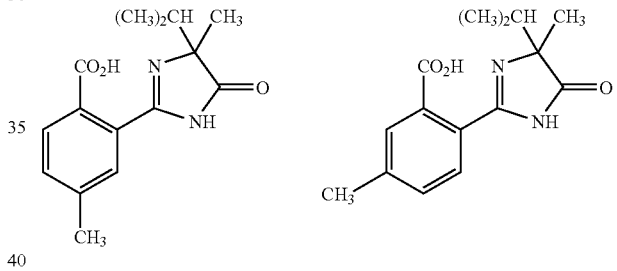

Reaction product comprising
(±)-6-(4-isopropyl-4-methyl-4-oxo-2-imidazolin-2-yl)-m-toluic acid and (±)-6-(4-isopropyl-4-methyl-4-oxo-2-imidazolin-2-yl)-p-toluic acid,
it also being possible to apply the respective methyl esters, which are known as imazamethabenzmethyl,
Pesticide Manual, 10th Edition 1994, pp. 582–584, B9) tralkoxydim

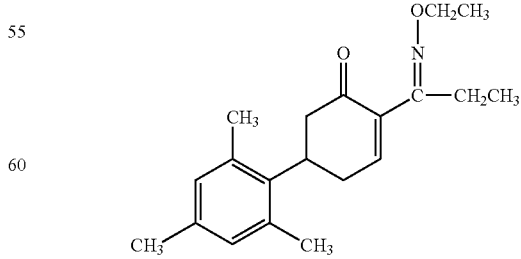

2-[1-(ethoxyimino)propyl]-3-hydroxy-5-mesitylcyclohex-2-enone

Pesticide Manual, 10th Edition 1994, pp. 995–996,

B10) difenzoquat,

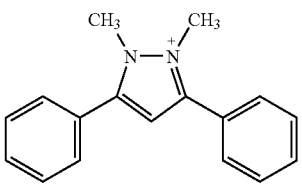

1,2-dimethyl-3,5-diphenylpyrazolium
for example also as difenzoquat metilsulfate, Pesticide Manual, 10th Edition 1994, pp. 330–331

B11) flamprop, flamprop-M,

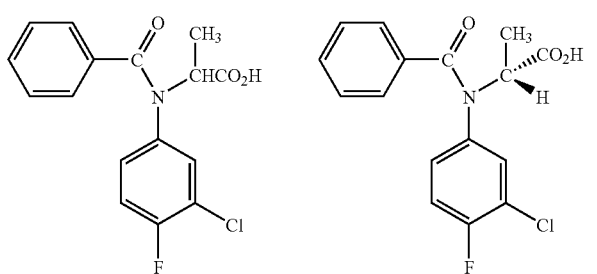

N-benzoyl-N-(3-chloro-4-fluorophenyl)-DL-alanine
N-benzoyl-N-(3-chloro-4-fluorophenyl)-D-alanine
comprising, inter alia, also flamprop-methyl, flamprop-M-methyl and flamprop-M-isopropyl, Pesticide Manual, 10th Edition 1994, pp. 464–465 and 466–468 and

B12) pendimethalin

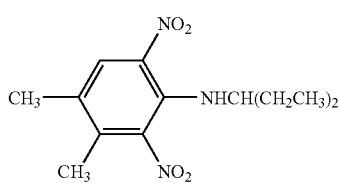

N-(1-ethylpropyl)-2,6-dinitro-3,4-xylidine Pesticide Manual, 10th Edition 1994, pp. 779–780

The compounds B1) to B12) are herbicides which are known, for example, from the literature indicated for the compound in question and which act selectively against grasses, specifically in cereals. Mention is made not only of the basic substance, whose formula is also indicated regularly for illustration purposes, but also of conventionally employed variations of the basic substances. For example B4) (clodinafop) is conventionally employed in the form of the propargyl ester and diclofop (B3)) as the methyl ester etc. If optically active forms of the type B compounds are customary, reference was also made of these forms (for example, inter alia, fenoxaprop-ethyl and fenoxaprop-P-ethyl etc.)

The compounds B1), B3) and B4) belong to the chemical class of the 2-(4-aryloxyphenoxy)propionic acids or to the ester derivatives. B2), B6) and B7) are ureas, while B8) is a representative of the imidazolinones, B9) a cyclohexanedione oxime, B11) an arylalanine and B12) a 2,6-dinitroaniline. Even though the representatives of this group vary quite considerably indeed with regard to their chemical structures, they nevertheless form a joint subgroup on the basis of their spectrum of action and because of the fact that they represent synergists for the compounds of the formula I.

In a further preferred embodiment of the invention, the herbicidally active combinations comprise, as type B herbicides, one or more herbicides which act selectively predominantly against grasses in maize and which are the group consisting of B13) nicosolfuron

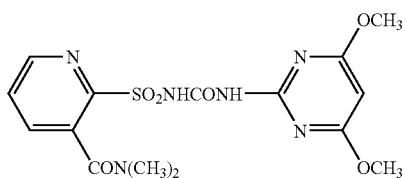

1-(4,6-dimethoxypyrimidin-2-yl)-3-(3-dimethylcarbamoyl-2-pyridylsulfonyl)urea
Pesticide Manual, 10th Edition 1994, pp. 734–735, B14) rimsulfuron

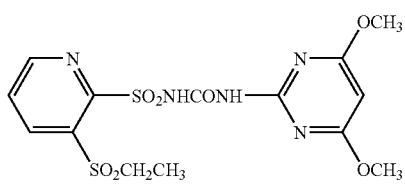

1-(4,6-dimethoxypyrimidin-2-yl)-3-(3-ethylsulfonyl-2-pyridylsulfonyl) urea
Pesticide Manual, 10th Edition 1994, pp. 904–905 and

B15) primisulfuron

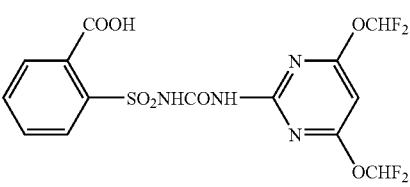

2-[4,6-bis (difluoromethoxy)pyrimidin-2-ylcarbamoylsulfamoyl]benzoic acid, which is predominantly employed as primisulfuron-methyl,
Pesticide Manual, 10th Edition 1994, pp. 829–830.

The abovementioned compounds B13) to B15) belong to the chemical group of the sulfonylureas. They differ structurally from the sulfonylureas of the formula I.

Particularly advantageous mixtures within the scope of the invention result when the combination according to the invention comprises, as type B compounds, diclofopmethyl, fenoxaprop-P-ethyl, isoproturon, mixtures of clodinafop-propargyl with cloquintocet-mexyl (known under the registered trademark Topik®), imazamethabenz-methyl, nicosulfuron and/or rimsulfuron.

Other compositions which are part of the invention are those which comprise type B herbicides from subgroup Bb). Particularly advantageously herbicides which act selectively against dicots in cereals and/or in maize are one or more herbicides from the group which embraces aryloxyalkylcarboxylic acids, hydroxybenzonitriles, diphenyl ethers, azoles and pyrazoles, diflufenican and bentazone.

Herbicides which are preferred amongst the aryloxyalkyl carboxylic acids which are possible are, in turn, those selected from the group consisting of B16) mecoprop, mecoprop-P

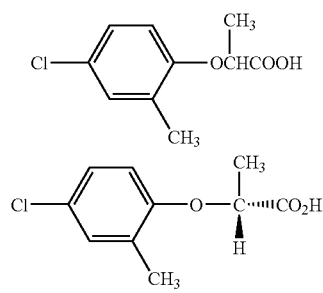

(RS)-2-(4-chloro-o-tolyloxy)propionic acid,
(R)-2-(4-chloro-o-tolyloxy)propionic acid,
Pesticide Manual, 10th Edition 1994, pp. 646–647 and 647–648,

B17) MCPA

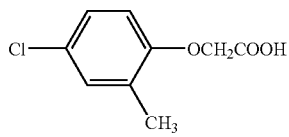

(4-chloro-2-methylphenoxy) acetic acid,
predominantly employed forms being, inter alia, MCPA-butotyl, MCPA-dimethylammonium, MCPA-iso-octyl, MCPA-potassium and MCPA-sodium,
Pesticide Manual, 10th Edition 1994, pp. 638–640, B18) dichlorprop, dichlorprop-P

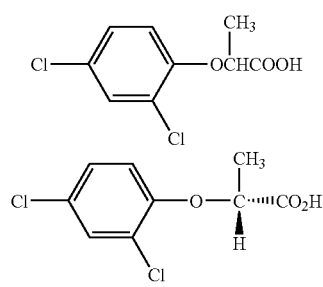

(RS)-2-(2,4-dichlorophenoxy)propionic acid,
(R)-2-(2,4-dichlorophenoxy)propionic acid,
other forms which are used being, inter alia, dichlorprop-butotyl, dichlorprop-ethylammonium, dichlorprop-iso-octyl and dichlorprop-potassium, Pesticide Manual, 10th Edition 1994, pp. 309–311 and 311–312,

B19) 2,4-D

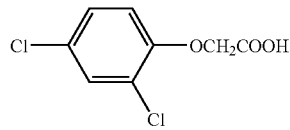

(2,4-dichlorophenoxy)acetic acid,
frequently employed forms: 2,4-D-butotyl, 2,4-D-butyl, 2,4-D-dimethylammonium, 2,4-D-diolamine, 2,4-D-iso-octyl, 2,4-D-isopropyl and 2,4-D-trolamine, Pesticide Manual, 10th Edition 1994, pp. 271–273, B20) dicamba

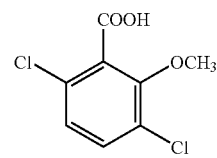

3,6-dichloro-o-anisic acid
applied, inter alia, in the form of dicamba-dimethylammonium, dicamba-potassium, dicamba-sodium and dicamba-trolamine,
Pesticide Manual, 10th Edition 1994, pp. 298–300 and B21) fluroxypyr

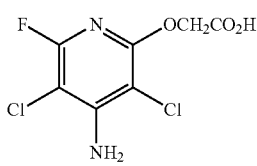

4-amino-3,5-dichloro-6-fluoro-2-pyridyloxyacetic acid,
other use form: fluroxypyr-meptyl, Pesticide Manual, 10th Edition 1994, pp. 505–507.

Also of particular interest are herbicidal compositions comprising hydroxybenzonitriles which act selectively against dicots in cereals and/or maize. These preferably include B22) ioxynil

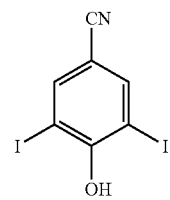

4-hydroxy-3,5-di-iodobenzonitrile,
frequent forms: ioxynil-octanoate and ioxynil-sodium, Pesticide Manual, 10th Edition 1994, pp. 598–600 and B23) bromoxynil

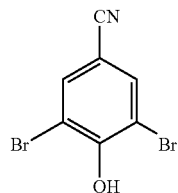

3,5-dibromo-4-hydroxy-benzonitrile,
frequently employed as bromoxynil-octanoate and bromoxynil-potassium,
Pesticide Manual, 10th Edition 1994, pp. 121–123.

Other advantageous compositions according to the invention are distinguished by the fact that they comprise, as type B) herbicides, one or more diphenyl ethers which act selectively against dicots in cereals and/or maize and which are selected from amongst the herbicides B24) bifenox

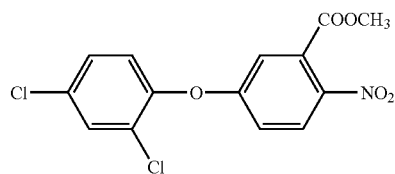

methyl-5-(2,4-dichlorophenoxy)-2-nitrobenzoate, Pesticide Manual, 10th Edition 1994, pp. 94–96, B25) fluoroglycofen

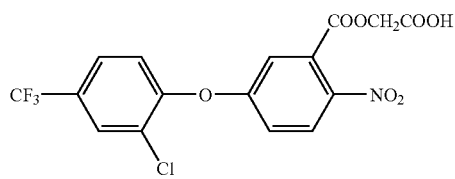

O-[5-(2-choro-α,α,α-trifluoro-p-tolyloxy)-2-nitrobenzoyl]glycolic acid,
other use form: Fluoroglycofen-ethyl,
Pesticide Manual, 10th Edition 1994, pp. 492–494, B26) acifluorfen

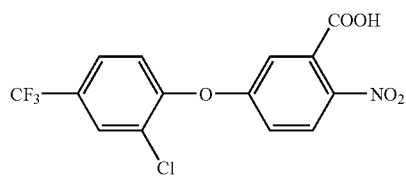

5-(2-chloro-α,α,α-trifluoro-p-tolyloxy)-2-nitrobenzoic acid,
also used in the form of acifluorfen-sodium, Pesticide Manual, 10th Edition 1994, pp. 12–13, B27) lactofen

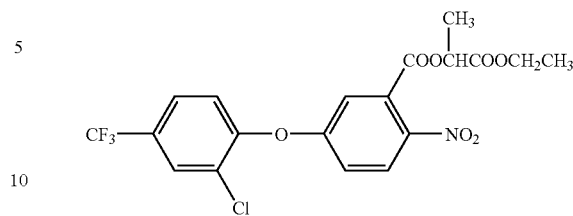

Ethyl O-[5-(2-chloro-α,α,α-trifluoro-p-tolyloxy)-2-nitrobenzoyl]-DL-lactate,
Pesticide Manual, 10th Edition 1994, pp. 623, B28) fomesafen

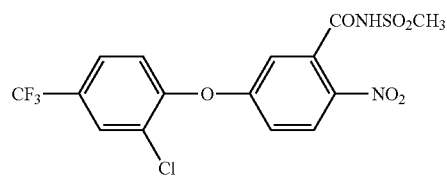

5-(2-chloro-α,α,α-trifluoro-p-tolyloxy)-N-methylsulfonyl-2-nitrobenzamide,
also employed in the form of fomesafen-sodium, Pesticide Manual, 10th Edition 1994, pp. 520–521 and B29) oxyfluorfen

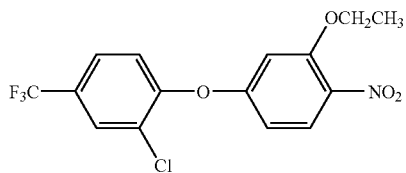

2-chloro-α,α,α-trifluoro-p-tolyl 3-ethoxy-4-nitro-phenyl ether,
Pesticide Manual, 10th Edition 1994, pp. 764–765.

Also of particular interest are furthermore herbicidal compositions which comprise, as type B compound, one or more azoles and pyrazoles which act selectively against dicots in cereals and/or maize and which are selected from the group consisting of the herbicides

B30) ET-751

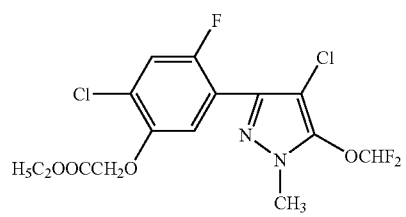

ethyl 2-chloro-5-(4-chloro-5-difluoromethoxy-1-methylpyrazol-3-yl)-4-fluorophenoxyacetate Pesticide Manual, 10th Edition 1994, pp. 400 and B31) azoles of the formula II

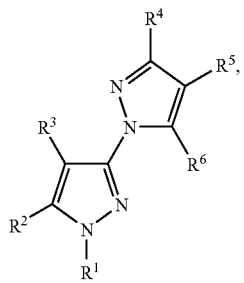

where

| | |
|---|---|
| $R^1$ | is $(C_1-C_4)$ alkyl, |
| $R^2$ | is $(C_1-C_4)$ alkyl, $(C_1-C_4)$ alkylthio or $(C_1-C_4)$ alkoxy, it being possible for each radical to be substituted by one or more halogen atoms, or |
| $R^1$ and $R^2$ | together form the group $(CH_2)_m$ where $m = 3$ or 4, |
| $R^3$ | is hydrogen or halogen, |
| $R^4$ | is hydrogen or $(C_1-C_4)$ alkyl, |
| $R^5$ | is hydrogen, nitro, cyano or one of the groups $-COOR^7$, $-C(=X)NR^7R^8$ or $-C(=X)R^{10}$, |
| $R^6$ | is hydrogen, halogen, cyano, $(C_1-C_4)$-alkyl, $(C_1-C_4)$ alkylthio or $-NR^{11}R^{12}$, |
| $R^7$ and $R^8$ | are identical or different and are hydrogen or $(C_1-C_4)$ alkyl, or |
| $R^7$ and $R^8$ | together with the nitrogen to which they are bonded form a saturated 5- or 6-membered carbocyclic ring, |
| $R^{10}$ | is hydrogen or $(C_1-C_4)$ alkyl, it being possible for the latter to be optionally substituted by one or more halogen atoms, and |
| $R^{11}$ and $R^{12}$ | are identical or different and are hydrogen, $(C_1-C_4)$ alkyl or $(C_1-C_4)$-alkoxycarbonyl, it being possible for |
| $R^{11}$ and $R^{12}$ | together with the nitrogen to which they are bonded to form a 3-, 5- or 6-membered carbocyclic or aromatic ring in which one carbon atom can optionally be replaced by an oxygen atom; | the azoles of the formula II being disclosed, inter alia, in WO 94/08999.

Also preferred as type B compound is

B32) diflufenican

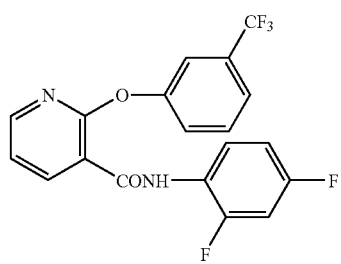

2' 4'-difluoro-2-(α,α,α-trifluoro-m-tolyloxy)nicotinanilide

Pesticide Manual, 10th Edition 1994, pp. 335–336.

A further advantageous embodiment of the invention is characterized in that a herbicidal composition comprises, as type B herbicide, B33) bentazone

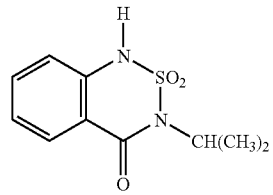

3-isopropyl-1H-2,1,3-benzothiadiazin-4 (3H)-one 2,2-dioxide,

Pesticide Manual, 10th Edition 1994, pp. 90–91.

A further advantageous embodiment of the invention is characterized in that a herbicidal composition comprises, as type B herbicide, phenyl propionates such as B51) carfentrazone

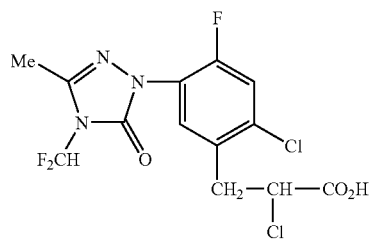

B52) carfentrazone-ethyl

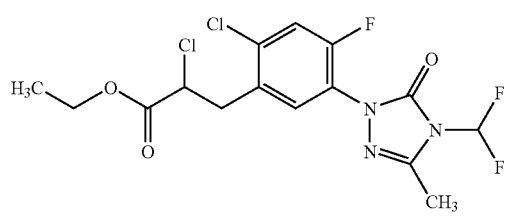

Very particularly suitable as component in a herbicidal composition according to the invention are, amongst the type B compounds which are selective in cereals and/or maize and active against dicots {subgroup Bb) comprising of the herbicidally active substances B16)-B33) and their customary derivatives}, MCPA, mecoprop, dicamba, fluroxypyr, diflufenican, ioxynil and/or fluoroglycofen.

A third subgroup of compounds whose admixture with type A compounds permits herbicidal compositions with outstanding characteristics to be obtained is subgroup Bc) of the herbicides which act selectively against grasses and dicots in cereals and/or maize. Type B substances with this profile of action are predominantly found in the chemical classes of the triazine derivatives, chloroacetanilides and sulfonylureas, which differ from the sulfonylureas given in formula I.

Preferred representatives are, inter alia, those which can predominantly be employed selectively against grasses and dicots in cereals and, if appropriate, in maize. These include, especially, the herbicidally active triazine derivatives and chloroacetanilides selected from the group consisting of the active substances B34) metolachlor

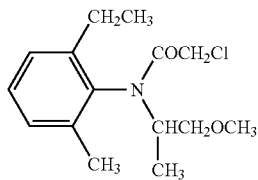

2-chloro-6'-ethyl-N-(2-methoxy-1-methylethyl) acet-o-toluidid,

Pesticide Manual, 10th Edition 1994, pp. 693–694,

B35) metribuzin

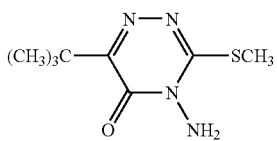

4-amino-6-tert-butyl-4,5-dihydro-3-methylthio-1,2,4-triazin-5-one

Pesticide Manual, 10th Edition 1994, pp. 699–700,

B36) atrazine

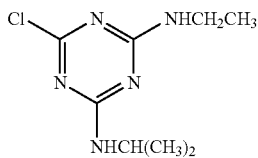

6-chloro-N-$^2$-ethyl-N-4-isopropyl-1,3,5-triazine-2,4-diamine

Pesticide Manual, 10th Edition 1994, pp. 51–52,

B37) terbuthylazine

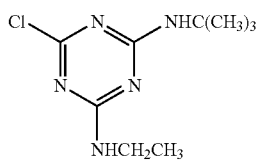

$N^2$ tert-butyl-6-chloro-N-$^4$-ethyl-1,3,5-triazine-2,4-diamine,

Pesticide Manual, 10th Edition 1994, pp. 960–961,

B38) alachlor

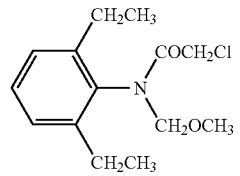

2-chloro-2',6'-diethyl-N-methoxymethylacetanilide, Pesticide Manual, 10th Edition 1994, pp. 21–22 and B39) acetochlor

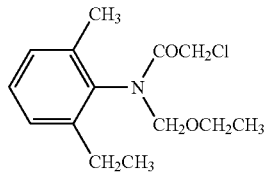

2-chloro-N-ethoxyethyl-6'-ethyl) acet-o-toluidid Pesticide Manual, 10th Edition 1994, pp. 10–11.

In an advantageous embodiment, the herbicidal compositions of the invention also exhibit, as type B component, one or more sulfonylureas which act selectively in cereals against grasses and dicots and, if appropriate, selectively in maize against grasses and dicots and which differ from the type A compounds.

Particularly preferred sulfonylureas of this type are, inter alia,

B40) amidosulfuron

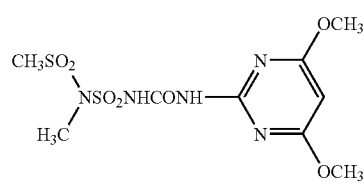

1-(4,6-dimethoxypyrimidin-2-yl)-3-mesyl (methyl)-sulfamoylurea,

Pesticide Manual, 10th Edition 1994, pp. 34–35,

B41) metsulfuron

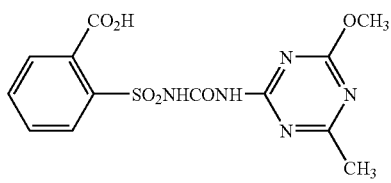

2-(4-methoxy-6-methyl-1,3,5-triazin-2-ylcarbamoyl-sulfamoyl)benzoic acid, conventionally employed in the form of metsulfuronmethyl, Pesticide Manual, 10th Edition 1994, pp. 701–702, B42) tribenuron

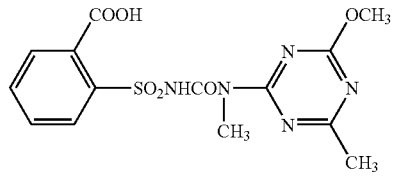

2-[4-methoxy-6-methyl-1,3,5-triazin-2-yl(methyl) carbamoylsulfamoyl]benzoic acid, conventionally employed in the form of tribenuron-methyl, Pesticide Manual, 10th Edition 1994, pp. 1010–1011, B43) thifensulfuron

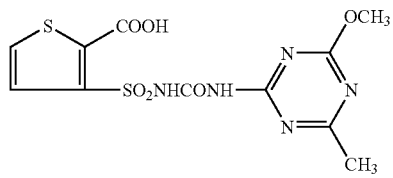

3-(4-methoxy-6-methyl-1,3,5-triazin-2-ylcarbamoylsulfamoyl) thiophene-2-carboxylic acid, usually used in the form of thifensulfuron-methyl, Pesticide Manual, 10th Edition 1994, pp. 976–978, B44) triasulfuron

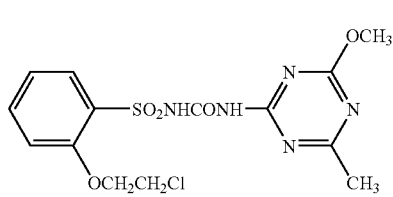

1-[2-(2-chloroethoxy) phenylsulfonyl]-3-(4-methoxy-6-methyl-1,3,5-triazin-2-yl)urea, Pesticide Manual, 10th Edition 1994, pp. 1005–1006, B45) chlorsulfuron

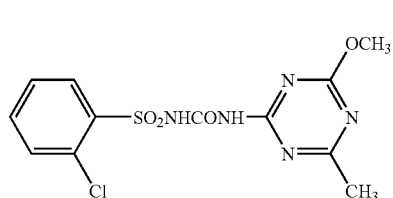

1-(2-chlorophenylsulfonyl)-3-(4-methoxy-6-methyl-1,2,5-triazin-2-yl)urea,

Pesticide Manual, 10th Edition 1994, pp. 203–205,

B46) prosulfuron or CGA-152005

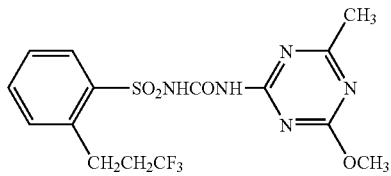

1-(4-methoxy-6-methyl-1,3,5-triazin-2-yl)-3-[2-(3,3,3-trifluoropropyl)phenylsulfonyl]urea, Pesticide Manual, 10th Edition 1994, pp. 865–866, and/or B47) Sulfonylureas of the formula III

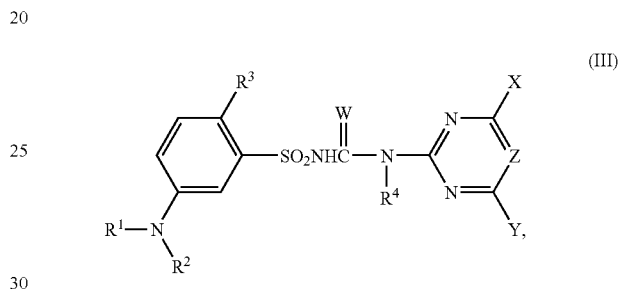

in which

| | |
|---|---|
| $R^1$ | is methyl, ethyl, n-propyl, i-propyl or allyl, |
| $R^2$ | is CO—$R^5$, COOR$^6$, CO—NR$^8$R$^9$, CS—NR$^{10}$R$^{11}$, SO$_2$R$^{14}$ or SO$_2$NR$^{15}$R$^{16}$, |
| $R^3$ | is COR$^{17}$, COOR$^{18}$, CONR$^{19}$R$^{20}$ or CO—ON=CR$^{22}$R$^{23}$, |
| $R^4$ | is hydrogen or (C$_1$–C$_4$) alkyl, |
| $R^5$ | is hydrogen, (C$_1$–C$_4$) alkyl, (C$_1$—C$_2$) haloalkyl, cyclopropyl, phenyl, benzyl or heteroaryl having 5 or 6 ring atoms, the last-mentioned 3 radicals being unsubstituted or substituted by one or more halogen atoms, |
| $R^6$ | is (C$_1$–C$_4$) alkyl, allyl, propargyl or cyclopropyl, |
| $R^8$ | is hydrogen, (C$_1$–C$_4$) alkyl, (C$_1$–C$_4$) haloalkyl or (C$_1$–C$_4$-alkoxy) carbonyl, |
| $R^9$—$R^{11}$ | independently of one another are identical or different and are H or (C$_1$–C$_4$) alkyl, |
| $R^{14}$ | is (C$_1$–C$_4$) alkyl, |
| $R^{15}$ and $R^{16}$ | independently of one another are identical or different and are hydrogen or (C$_1$–C$_4$) alkyl, |
| $R^{17}$ | is hydrogen, (C$_1$–C$_4$) alkyl, (C$_1$–C$_4$) haloalkyl, (C$_3$–C$_6$) cycloalkyl, phenyl or heteroaryl, the last-mentioned two radicals being unsubstituted or substituted, |
| $R^{18}$ | is hydrogen, (C$_1$–C$_4$) alkyl, (C$_2$–C$_6$)-alkenyl or (C$_2$–C$_6$) alkynyl, the last-mentioned three radicals being unsubstituted or substituted by one or more radicals selected from the group consisting of halogen, (C$_1$–C$_4$) alkoxy, (C$_1$–C$_4$) alkylthio and NR$^{31}$R$^{32}$, or is (C$_3$–C$_6$) cycloalkyl or (C$_3$–C$_6$) cycloalkyl-(C$_1$–C$_3$) alkyl, |
| $R^{19}$ | is analogous to $R^8$, |
| $R^{20}$ | is analogous to $R^9$, |

-continued

| | |
|---|---|
| $R^{22}$ and $R^{23}$ | independently of one another are identical or different and are hydrogen or $(C_1-C_2)$ alkyl, |
| $R^{31}$ and $R^{32}$ | independently of one another are identical or different and are hydrogen or $(C_1-C_4)$ alkyl, |
| W | is oxygen or sulfur, |
| X | is $(C_1-C_4)$ alkyl, $(C_1-C_4)$ alkoxy, $(C_1-C_4)$-haloalkyl, $(C_1-C_4)$ alkylthio, halogen or mono- or di$(C_1-C_2$-alkyl) amino, |
| Y | is $(C_1-C_4)$ alkyl, $(C_1-C_4)$ alkoxy, $(C_1-C_4)$-haloalkyl or $(C_1-C_4)$ alkylthio, and |
| Z | is CH or N. |

The sulfonylureas of the formula III are disclosed in WO 94/10154.

In yet another preferred embodiment, the herbicidal compositions of the invention furthermore exhibit, as type B component,

B48) K1H-2023

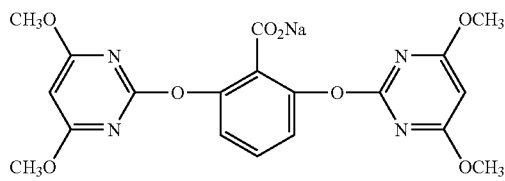

Sodium 2,6-bis[(4,6-dimethoxypyrimidin-2-yl)oxy]-benzoate,

Pesticide Manual, 10th Edition 1994, pp. 620.

Very particularly suitable as component of a herbicidal composition according to the invention amongst the type B compounds which are selective in cereals and/or maize and act against grasses and dicots {subgroup Bc) comprising the herbicidally active substances B34)–B48) and their customary derivatives} are atrazine, metsulfuron-methyl, tribenuron-methyl and/or amidosulfuron.

A fourth subgroup of compounds whose admixture with type A compounds allows herbicidal compositions with superadditive activity to be obtained is subgroup Bd) of the herbicides which are active against grass weeds and broad-leaved weeds and are non-selective in non-crop areas and/or selective in transgenic cultures. Type B substances which are thus described are, inter alia, B49) glufosinate, glufosinate-P

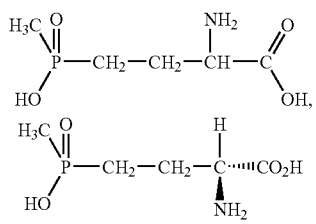

4-[hydroxy(methyl)phosphinoyl]-DL-homoalanine,
4-[hydroxy(methyl)phosphinoyl]-L-homoalanine,
which are in each case preferably used in the form of glufosinate-ammonium or glufosinate-P-ammonium, Pesticide Manual, 10th Edition 1994, pp. 541–542 and/or B50) glyphosate

N-(phosphonomethyl)glycine,
which is preferably employed in the form of glyphosate-isopropylammonium,
glyphosate-sesquisodium and glyphosate-trimesium, Pesticide Manual, 10th Edition 1994, pp. 542–544.

Combinations of the active substances A+B show superadditive effects, i.e. the herbicidal compositions according to the invention allow the rate of application to be reduced and/or the safety margin especially in cereals and/or maize crops to be increased while retaining equally good control of the harmful plants. Achieving both makes sense economically and ecologically. The choice of the amounts of components A+B to be employed, the ratio of component A: component B and the order in time in which the components are applied depend on a wide variety of factors, as does, for example, the formulation to be selected. Not insignificant in this context are, inter alia, the type of the components in the mixture, the development stage of the broad-leaved or grass weeds, the weed spectrum to be controlled, environmental factors, climatic conditions, soil conditions etc.

In a very particularly preferred embodiment according to the invention, herbicidal compositions according to the invention are characterized in that they exhibit a synergistically active content of combination of the compounds of the formula I or salts thereof (type A compounds) with compounds from group B. It must be emphasized, in particular, that even in combinations with rates of application or weight ratios of A:B where synergism cannot be detected easily in each case—for example because the individual compounds are usually employed in the combination in very different rates of application or else because control of the harmful plants is already very good as a result of the individual compounds—a synergistic action is, as a rule, inherent in the herbicidal compositions of the invention.

As already mentioned, the weight ratios A:B of the combined herbicides, and also their rates of application, can vary within wide limits. Preferred compositions within the scope of the invention are those which comprise compounds of the formula I or salts thereof (type A compounds) and compounds from group B in a weight ratio of 1:2500 to 20:1.

The following weight ratios are preferably employed:

| | Mixing ratios A:B | |
|---|---|---|
| Type B compounds | standard | preferred |
| Ba) Grass herbicides in cereals {e.g. B1)–B12)} | 1:500 to 1:1 | 1:200 to 1:2 |
| Ba) Grass herbicides in maize {e.g. B13)–B15)} | 1:30 to 8:1 | 1:10 to 1:1 |
| Bb) Dicot herbicides in cereals and maize {e.g. B16)–B21)} | 1:1500 to 1:1 | 1:500 to 1:10 |
| Bb) Dicot herbicides | 1:500 to 1:1 | 1:200 to 1:3 |

-continued

| Type B compounds | Mixing ratios A:B standard | preferred |
|---|---|---|
| in cereals and maize {e.g. B22) and B23)} Bb) Dicot herbicides in cereals and maize {e.g. B24)–B29)} | 1:500 to 8:1 | 1:300 to 2:1 |
| Bb) Dicot herbicides in cereals and maize {e.g. B30) and B31)} | 1:20 to 20:1 | 1:10 to 10:1 |
| Bb) Dicot herbicides in cereals and maize {e.g. B32)} | 1:250 to 1:1 | 1:100 to 1:3 |
| Bb) Dicot herbicides in cereals and maize {e.g. B33)} | 1:2500 to 1:5 | 1:2000 to 1:10 |
| Bc) Grass and dicot herbicides in cereals and/or maize {e.g. B34)–B39)} | 1:2500 to 1:2 | 1:2000 to 1:4 |
| Bc) Grass and dicot herbicides in cereals and/or maize {e.g. B30)–B48)} | 1:40 to 20:1 | 1:20 to 10:1 |
| Bd) Broad - spectrum herbicides which are non-selective, or only selective in transgenic crops {e.g. B49) to B50)} | 1:1500 to 1:2 | 1:1000 to 1:10 |

The rates of application of herbicide A in the active substance combinations according to the invention are between 0.1 and 100 g of a.i./ha (a.i.=active ingredients, i.e. rate of application based on the active substance), preferably between 2 and 40 g of a.i./ha.

As a rule, the rates of application of type B compounds in the mixtures according to the invention are:

| Type B compounds | Rates of application in g of a.i./ha standard | preferred |
|---|---|---|
| Ba) Grass herbicides in cereals {e.g. B1)–B12)} | 1 10 to 4000 | 50 to 1000 |
| Ba) Grass herbicides in maize {e.g. B13)–B15)} | 5 to 60 | 5 to 30 |
| Bb) Dicot herbicides in cereals and maize {e.g. B16)–B21)} | 50 to 3000 | 100 to 2000 |
| Bb) Dicot herbicides in cereals and maize {e.g. B22) and B23)} | 50 to 1000 | 100 to 500 |
| Bb) Dicot herbicides in cereals and maize {e.g. B24)–B29)} | 5 to 1000 | 10 to 500 |
| Bb) | 3 to 25 | 5 to 20 |
| Dicot herbicides in cereals and maize {e.g. B30) and B31)} Bb) | 50 to 500 | 100 to 250 |
| Dicot herbicides in cereals and maize {e.g. B32)} Bb) | 500 to 2500 | 750 to 2000 |
| Dicot herbicides in cereals and maize {e.g. B33)} Bc) | 100 to 5000 | 250 to 2500 |
| Grass and dicot herbicides in cereals and/or maize {e.g. B34)–B39)} Bc) | 2 to 80 | 5 to 50 |
| Grass and dicot herbicides in cereals and/or maize {e.g. B40)–B48)} Bd) | 100 to 3000 | 100 to 1000 |
| Broad - spectrum herbicides which are non-selective, or only selective in transgenic crops {e.g. B49) and B50)} | | |

The active substance combinations according to the invention can exist either as mixed formulations of the two components, which are then applied in the customary manner in the form of a dilution with water, or else prepared as so-called tank mixes by joint dilution with water of the components which are formulated separately.

The active substances of types A and B can be formulated in various ways, depending on the prevailing biological and/or chemico-physical parameters. Suitable formulations which are possible are, for example:

wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-dressing products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual types of formulations are known in principle and are described, for example, in: Winnacker-Küachler, "Chemische Technologie" [Chemical Technology], Volume 7, C. Hauser Verlag Munich, 4th Edition 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J.; H. v. Olphen "Introduction to Clay Colloid Chemistry", 2nd Ed., J. Wiley & Sons, N.Y.;

Marsden "Solvents Guide, 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflachenaktive Äthylenoxidaddukte" [Surface-active ethylene oxide adducts], Wiss. Verlagsgesellschaft, Stuttgart 1976; Winnacker-Küchler "Chemische Technologie" [Chemical Technology], Volume 7, C. Hauser Verlag Munich, 4th Edition 1986.

Based on these formulations, it is also possible to prepare combinations with other pesticidally active substances, herbicides, insecticides, fungicides and antidotes, safeners, fertilizers and/or growth regulators, for example in the form of readymix or a tank mix.

The herbicide combinations of the invention are particularly advantageously prepared by formulating the compounds of the formula I or salts thereof (type A compounds) with one or more type B compounds analogously to a customary crop protection formulation from the group comprising water-soluble wettable powders (WP), waterdispersible granules (WDG), water-emulsifiable granules (WEG), suspoemulsions (SE) and oil suspension concentrates (SC).

Wettable powders are preparations which are uniformly dispersible in water and which, besides the active substances, also comprise ionic and/or nonionic surfactants (wetting agents, dispersants), for example polyoxyethylated alkylphenols, polyoxyethylated fatty alcohols and fatty amines, fatty alcohol polyglycol ether sulfates, alkanesulfonates or alkylarylsulfonates, sodium lignosulfonate, sodium 2,2'-dinaphthylmethane-6,6'-disulfonate, sodium dibutylnaphthalenesulfonate or else sodium oleylmethyltauride, in addition to a diluent or inert substance.

Emulsifiable concentrates are prepared by dissolving the active substance, or active substances, in an organic solvent, for example butanol, cyclohexanone, dimethylformamide, xylene or else higher-boiling aromatics or hydrocarbons with the addition of one or more ionic and/or non-ionic surfactants (emulsifiers).

Examples of emulsifiers which can be used are: calcium alkylarylsulfonates, such as calcium dodecylbenzene sulfonate, or non-ionic emulsifiers such as fatty acid polyglycol esters, alkylaryl polyglycol ethers, fatty alcohol polyglycol ethers, propylene oxide/ethylene oxide condensates (for example block copolymers), alkyl polyethers, sorbitan fatty acid esters, polyoxyethylene sorbitan fatty acid esters or other polyoxyethylene sorbitan esters.

Dusts are obtained by grinding the active substance, or active substances, with finely divided substances, for example talc, natural clays such as kaolin, bentonite and pyrophyllite, or diatomaceous earth.

Granules can be prepared either by spraying the active substance, or active substances, on to adsorptive, granulated inert material or by applying active substance concentrates to the surface of carriers such as sand, kaolinites or granulated inert material with the aid of binders, for example polyvinyl alcohol, sodium polyacrylate or else mineral oils. Water-dispersible granules are prepared, as a rule, by the customary processes such as spray drying, fluidized-bed granulation, disk granulation, mixing using high-speed mixers and extrusion without solid inert material. Suitable active substances can also be granulated in the manner which is customary for the preparation of fertilizer granules, if desired in the form of a mixture with fertilizers.

As a rule, the agrochemical preparations according to the invention comprise 0.1 to 99% by weight, in particular 2 to 95% by weight, of active substances of types A and B besides customary formulation auxiliaries.

The concentrations of the active substances A+B in the formulations can vary. In wettable powders, the active substance concentration is, for example, approximately 10 to 95% by weight, the remainder to 100% being composed of customary formulation components. In the case of emulsifiable concentrates, the active substance concentration can be from approximately 1 to 85% by weight, preferably 5 to 80% by weight. Formulations in the form of dusts comprise approximately 1 to 25% by weight, in most cases 5 to 20% by weight, of active substances, sprayable solutions approximately 0.2 to 25% by weight, preferably 2 to 20% by weight, of active substances. In granules, such as dispersible granules, the active substance content depends partly on whether the active compound is in liquid or solid form and on which granulation auxiliaries and fillers are used. As a rule, the content in the water-dispersible granules is between 10 and 90% by weight.

Besides, the abovementioned active substance formulations comprise, if appropriate, the adhesives, wetting agents, dispersants, emulsifiers, penetrants, preservatives, antifreeze agents, solvents, fillers, colorants, carriers, antifoams, evaporation inhibitors and pH- and viscosity-regulators which are customary in each case.

To increase the tolerance and/or selectivity of the herbicide combinations according to the invention even further, it is advantageous to apply them together with safeners or antidotes, either jointly in a mixture or at different points in time. The compounds which are suitable as safeners or antidotes for the combinations according to the invention are, for example, disclosed in EP-A-333 131 (ZA-89/1960), EP-A-269 806 (U.S. Pat. No. 4,891,057), EP-A-346 620 (AU-A-89/34951) and in international patents PCT/EP 90/01966 (WO-91/08202) and PCT/EP 90/02020 (WO-91/078474) and in the literature cited therein or can be prepared by processes described in these publications.

Other suitable safeners are known from EP-A-94 349 (U.S. Pat. No. 4,902,304), EP-A-191 736 (U.S. Pat. No. 4,881,966) and EP-A-0 492 366 and from the literature cited in these publications. Particularly preferred antidotes or safeners are, inter alia, compounds of the dichlorophenylpyrazoline-3-carboxylic acid type, dichlorophenylpyrazolecarboxylic acid derivatives, compounds of the triazolecarboxylic acid type, compounds of the 5-benzyl-or, 5-phenyl-2-isoxazoline-3-carboxylic acid type, compounds of the 8-guinolineoxyacetic acid type, compounds of the (5-chloro-8-quinolinoxy)malonic acid type and active substances of the phenoxyacetic- or propionic acid derivative or aromatic carboxylic acid type. All of the abovementioned compounds are described in EP-A-0 640 587, to which reference is made for disclosure purposes. The abovementioned application not only mentions the above-described safeners and antidotes for compounds of the formula I, but also mixtures with standard herbicides. This application, however, lacks, on the one hand, a necessary individual enumeration of the compounds of the formula I, since they are embraced by a very much broader formula in EP-A-0 640 587, and, on the other hand, nothing is mentioned about the surprising superadditive increase in action of the combinations disclosed in the present application.

For use, the formulations, which are in commercially available form, are, if appropriate, diluted in the customary manner, for example using water in the case of wettable powders, emulsifiable concentrates, dispersions and water-dispersible granules. Preparations in the form of dusts, soil granules, granules for broadcasting and sprayable solutions are conventionally not diluted further with other inert substances prior to use.

The invention also relates to a method of controlling undesirable plants, which comprises applying a herbicidally active amount of a combination according to the invention of active substances A+B to these plants or to the area under cultivation. The active substances can be applied to the plants, to parts of the plants, to seeds of the plants or to the area under cultivation. In a preferred variant of the method, the compounds of the formula (I) or salts thereof (type A compounds) are applied at rates of 0.1 to 100 g of a.i./ha, preferably 2 to 40 g of a.i./ha, while the rates for the type B compounds are from 1 to 5000 g of a.i./ha. Application of the active substances of types A and B simultaneously or at separate points in time in a weight ratio of 1:2500 to 20:1 is preferred. The joint application of the active substances in the form of tank mixes is furthermore particularly preferred, the optimally formulated concentrated formulations of the individual active substances are jointly mixed with water in the tank and the resulting spray mixture is applied.

Since the tolerance of the combinations according to the invention by crops is extremely good while simultaneously controlling the harmful plants to a very high degree, they can be regarded as selective. In a preferred embodiment, herbicidal compositions comprising the active substance combinations according to the invention are therefore employed for selectively controlling undesirable plants. The method of selectively controlling harmful plants when using the type B) components from subgroups Ba) to Bc) is particularly advantageous when the herbicidal compositions of the invention are employed in crops such as cereals, maize, rice, sugar cane, in plantation crops, in grassland or in pastures.

The type A components used by themselves pre-emergence or post-emergence in cereals, rice and maize, in non-crop areas and in plantation crops already control a fairly broad spectrum of annual and perennial broad-leaved weeds, grass weeds and Cyperaceae.

The spectrum of action of the type A compounds is further improved by combining them with the type B components mentioned in the invention.

Thus, the compounds B1) to B12) complement and enhance, inter alia, the action when controlling grass weeds in cereals and, in some cases, also the action against broad-leaved weeds in cereals, in each case both pre- and post-emergence.

The sulfonylureas from subgroup Ba) (compounds B13) to B15)) are mainly used for an even more efficient control of grass weeds and broad-leaved weeds, mainly post-emergence in maize.

The components B16) to B21) of the group Bb) are in most cases growth regulator herbicides, which improve the action of the type A compounds in a large number of agricultural crops (preferably cereals and maize), especially when controlling broad-leaved weeds and Cyperaceae. They are preferably employed post-emergence.

Compounds B22) and B23) are herbicidally active substances which mainly improve the efficacy of weed control in maize and cereals. In most cases, they are employed post-emergence. The nitrodiphenyl ethers B24) to B29) are employed both pre- and post-emergence. They are used to improve the efficacy in cereals, rice, maize, but also soya beans.

The azoles and pyrazoles from subgroup Bb) (e.g. B30) and B31)) can be employed particularly advantageously at comparatively low rates in the post-emergence control of dicotyledon weeds in cereals. B33) improves the spectrum of action of the combinations according to the invention pre- and post-emergence when controlling weeds in cereals and other crop species, while B33) is a herbicidally active substance which is employed post-emergence for controlling weeds in a large number of agricultural crop plants.

The triazines and chloroacetanilides from subgroup Bc) (e.g. B34) to B39)) are widely used active substances which can be employed both pre- and post-emergence for improving the efficacy of the type A compounds in the control of grass weeds and broad-leaved weeds, especially in maize, but in some cases also in cereals, in non-crop areas or in plantation crops.

Finally, compounds B40) to B48) (subgroup Bc)) are used, in the invention, preferably for controlling broad-leaved is weeds—in some cases also grass weeds—in cereals and in some cases in maize but also in potatoes, in grassland or in non-crop areas post-emergence, but in some cases also pre-emergence.

Depending on the nature of component B, the herbicidal combinations according to the invention can advantageously be used for controlling undesirable plants even in non-crop areas and/or in transgenic crops such as maize, soya, cereals, rice and others. Particularly suitable for this purpose are the components from group Bd).

In this context, the term non-crop areas not only embraces paths, squares, industrial complexes and rail-tracks which must regularly be kept free from weeds, rather, plantation crops also come under this generic term within the scope of the invention. Accordingly, the combinations according to the invention (especially those comprising the components from subgroup Bd)), which control a wide spectrum of weeds ranging from annual and perennial weeds such as, for example, *Agropyron, Paspalum, Cynodon, Imperata* via *Pennisetum, Convolvulus* and *Cirsium* to *Rumex* and others can be applied for the selective control of harmful plants in plantation crops such as oil palm, coconut palm, india-rubber tree, citrus, pineapple, cotton, coffee, cocoa and the like and also in fruit growing and viticulture. Equally, the combinations according to the invention can be employed in arable crops using the no-till or zero-till method. As already mentioned, however, they can also be used in non-crop areas in the strict sense, i.e. non-selectively in paths, squares, etc., to keep these areas free from undesirable vegetation. However, the components from group Bd), which are non-selective per se, not only become selective herbicides when the tolerance of the crop plants is appropriate, but combinations according to the invention are also selective when used in so-called transgenic crops. Transgenic crops are plants which have been genetically manipulated to become resistant to herbicides which are non-selective per se. Such altered crop plants such as, for example, maize, cereals or soya beans, subsequently permit the selective use of combinations with B49) or B50).

To conclude, it can be said that superadditive (=synergistic) effects are observed when 4-iodo-2-[3-(4-methoxy-6-methyl-1,3,5-triazin-2-yl)ureidosulfonyl]benzoic esters and/or salts thereof are used together with one or more active substances from group B. The activity in the combinations exceeds the activity of the individual products when applied alone.

These effects permit
- the rate of application to be reduced,
- a broader spectrum of broad-leaved weeds and grass weeds to be controlled,
- more rapid and more reliable action,
- longer long-term action,
- complete control of the harmful plants with only one or few applications, and
- the application period of the active substances in combination to be extended.

The abovementioned properties are required under realistic weed control conditions to keep agricultural tracts free from undesirable competitors and thus to safeguard, or increase, quality and quantity of the yields. The combinations according to the invention markedly exceed the prior art with regard to the above-described characteristics.

The examples which follow are intended to illustrate the invention:

1. FORMULATION EXAMPLES a) A dust is obtained by mixing 10 parts by weight of an active substance combination according to the invention and 90 parts by weight of talc as inert substance and comminuting the mixture in a hammer mill.

b) A wettable powder which is readily dispersible in water is obtained by mixing 25 parts by weight of active substances A+B, 64 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

c) A dispersion concentrate which is readily dispersible in water is obtained by mixing 20 parts by weight of active substances A+B with 6 parts by weight of alkylphenol polyglycol ether (®Triton X 207), 3 parts by weight of isotrideconol polyglycol ether (8 EO) and 71 parts by weight of paraffinic mineral oil (boiling range for example approximately 255 to 277° C.) and grinding the mixture in a bowl mill to a fineness of below 5 microns.

d) An emulsifiable concentrate is obtained from 15 parts by weight of cyclohexanone as the solvent and 10 parts by weight of oxethylated nonylphenol as the emulsifier.

e) Water-dispersible granules are obtained by mixing 75 parts by weight of active substances A+B,
    10 parts by weight of calcium lignosulfonate,
    5 parts by weight of sodium lauryl sulfate,
    3 parts by weight of polyvinyl alcohol and
    7 parts by weight of kaolin,
    grinding the mixture in a pinned-disk mill and granulating the powder in a fluidized bed by spraying on water as the granulation liquid.

f) Water-dispersible granules are also obtained by homogenizing and precomminuting, in a colloid mill, 25 parts by weight of active substances A+B,
    5 parts by weight of sodium 2,2'-dinaphthylmethane-6,6'-disulfonate,
    2 parts by weight of sodium oleoylmethyltaurinate,
    1 part by weight of polyvinyl alcohol,
    17 parts by weight of calcium carbonate and
    50 parts by weight of water, subsequently grinding the mixture in a bead mill and atomizing and drying the resulting suspension in a spray tower by means of a single-substance nozzle.

g) Extruder granules are obtained by mixing 20 parts by weight of active substances A+B, 3 parts by weight of sodium lignosulfonate, 1 part by weight of carboxymethylcellulose and 76 parts by weight of kaolin, grinding the mixture and moistening it with water. This mixture is extruded and subsequently dried in a stream of air.

2. BIOLOGICAL EXAMPLES

The examples given below were performed in the greenhouse and, in some cases, in field trials.

Field Trials

The herbicides, or combinations, were applied in cereals after the weeds had emerged naturally using plot sprayers. After application, the results, such as damage to the crop plants and effect on broad-leaved weeds/grass weeds were assessed by means of visual scoring. The herbicidal action was assessed qualitatively and quantitatively by comparing untreated and treated plots on the basis of the effect on plant growth and the development of chloroses and necroses down to the complete destruction of the weeds (0–100%). The application was effected when the crop plants and weeds were in the 2–4 leaf stage. The test was evaluated approximately 4 weeks after application.

Greenhouse Experiments

In the greenhouse experiments, the crop plants and broadleaved weeds/grass weeds were grown in No. 13 pots and treated in the 2–4 leaf stage. The pots were subsequently placed in the greenhouse under good growth conditions (temperature, atmospheric humidity, water supply).

The assessments were carried out similarly to those in the field trials, i.e. visual scoring of the treated plants in comparison with untreated control variants. These assessments were carried out 3 weeks after applying the test preparations and their combinations. The experiments had been set up in two replications.

Assessment of the Combination Effects in the Examples

To assess the combination effects, the activities of the individual components were added and compared with the activity of the mixtures in equal doses. It was frequently observed that the efficacies of the combinations exceeded the total of the individual activities.

In cases with less clear effects, the expected value was calculated using Colby's formula and compared with the empirically determined result. The calculated efficacy of a combination which is expected in theory is determined is using S.R. Colby's formula:

"Calculation of synergistic and antagonistic responses of herbicide combinations", Weeds 15 (1967), pages 20 to 22.

In the case of two-way combinations, this formula reads:

$$E = X + Y - \frac{X \cdot Y}{100}$$

and in the case of the combination of three herbicidally active substances, analogously:

$$E = X + Y + Z + \frac{X \cdot Y \cdot Z}{10000} - \frac{XY + XZ + YZ}{100}$$

where
X=% damage caused by herbicide A at a rate of ×kg a.i./ha;
Y=% damage caused by herbicide B at a rate of y kg a.i./ha;
Z=% damage caused by a further herbicide C at a rate of z kg a.i./ha;
E=expected value, i.e. expected damage caused by herbicides A+B (or A+B+C) at x+y (or x+y+z) kg a.i./ha.

Synergistic effects were assumed to be when the empirical value exceeded the expected value. In the case of combinations with individual components with the same active substances, comparisons via the total formula were also possible.

However, in most cases, the synergistically increased action is so pronounced that Colby's criterium can be dispensed with; in this case, the activity of the combination clearly exceeds the formal (numerical) total of the activities of the individual substances.

Particular mention must be made of the fact that an assessment of the synergism in the active substances employed must take into consideration the great differences in rates in which the individual active substances are applied. Thus, it does not make sense to compare the activities of the active substance combinations and the individual active substances at in each case identical application rates. Other savings according to the invention in the amount of active substance only become apparent from the superadditive increase in action when using combined rates or from the reduction in the rates of the two individual active substances in the combinations in comparison with the individual active substances while achieving identical effects in each case.

TABLE 1

| Active substance(s) | g of a.i./ha | PHACA % control | APESV % control | TRZAW % damage |
|---|---|---|---|---|
| A) | 3 | 0 | 85 | 0 |
|  | 5 | 15 | 93 | 0 |
|  | 10 | 35 | 97 | 0 |
|  | 20 | 53 | 98 | 0 |
| B3) | 225 | 0 | 0 | 0 |
|  | 450 | 0 | 0 | 0 |
|  | 900 | 0 | 8 | 0 |
| A) + B3) | 3 + 450 | 90 (0 + 0) | 97 (85 + 0) | 0 |
|  | 5 + 450 | 90 (15 + 0) | 97 (93 + 0) | 0 |

PHACA = *Phalaris canariensis*
APESV = *Apera spica venti*
TRZAW = *Triticum aestivum*l
A) = sodium salt of methyl 4-iodo-2-[3-(4-methoxy-6-methyl-1,3,5-triazin-2-yl)ureidosulfonyl]benzoate
B3) = diclofop-methyl
( ) = % efficacy of individual active substances

TABLE 2

| Active substance(s) | g of a.i./ha | LOLMU % control | PHACA % control | TRZAW % damage |
|---|---|---|---|---|
| A) | 3 | 0 | 0 | 0 |
|  | 5 | 5 | 15 | 0 |
|  | 10 | 10 | 35 | 0 |
|  | 20 | 48 | 53 | 0 |
| B1) | 18 | 0 | 0 | 0 |
|  | 37 | 0 | 0 | 0 |
|  | 75 | 8 | 60 | 0 |
| A) + B1) | 3 + 37 | 58 (0 +0) | 88 (0 + 0) | 0 |
|  | 5 + 37 | 83 (5 + 0) | 97 (15 + 0) | 0 |
|  | 10 + 37 | 85 (10 + 0) | 99 (35 + 0) | 0 |
| B5) | 10 | 0 | 0 | 0 |
|  | 20 | 0 | 0 | 0 |
|  | 40 | 5 | 5 | 0 |
| A) + B5) | 3 + 20 | 75 (0 + 0) | 70 (0 + 0) | 0 |
|  | 5 + 20 | 85 (5 + 0) | 80 (15 + 0) | 0 |
|  | 10 + 10 | 81 (10 + 0) | 78 (35 + 0) | 0 |

LOLMU = *Lolium multiflorum*
PHACA = *Phalaris canariensis*
TRZAW = *Triticum aestivum*
A) = sodium salt of methyl 4-iodo-2-[3-(4-methoxy-6-methyl-1,3,5-triazin-2-yl)ureidosulfonyl]benzoate
B1) = Puma S ® = mixture of fenoxaprop-P-ethyl and the safener fenchlorazole-ethyl = 1-(2,4-dichlorophenyl)-5-(trichloromethyl-1H-1,2,4-triazole-3-carboxyethyl ester, ratio 2:1
B5) = Topik ® = mixture of clodinafop-propargyl and the safener cloquintocet-methyl, ratio 4:1
( ) = % efficacy of individual active substances

TABLE 3

| Active substance(s) | g of a.i./ha | LOLMU % control | PHACA % control | TRZAW % damage |
|---|---|---|---|---|
| A) | 3 | 0 | 0 | 0 |
|  | 5 | 5 | 15 | 0 |
|  | 10 | 10 | 35 | 0 |
|  | 20 | 48 | 53 | 0 |
| B2) | 375 | 0 | 0 | 0 |
|  | 750 | 0 | 0 | 0 |
|  | 1500 | 0 | 50 | 0 |
| A) + B2) | 3 + 1500 | 20 (0 + 0) | 80 (0 + 50) | 0 |
|  | 5 + 1500 | 43 (5 + 0) | 85 (15 + 50) | 0 |
|  | 10 + 1500 | 55 (10 + 0) | 83 (35 + 50) | 0 |
| B8) | 375 | 0 | 0 | 0 |
|  | 750 | 0 | 0 | 0 |
|  | 1500 | 20 | 13 | 5 |
| A) + B8) | 3 + 750 | 93 (0 + 0) | 99 (0 + 0) | 5 |
|  | 10 + 375 | 93 (10 + 0) | 99 (35 + 0) | 5 |

LOLMU = *Lolium multiflorum*
PHACA = *Phalaris canariensis*
TRZAW = *Triticum aestivum*
A) = sodium salt of methyl 4-iodo-2-[3-(4-methoxy-6-methyl-1,3,5-triazin-2-yl)ureidosulfonyl]benzoate
B2) = isoproturon (Arelon ® )
B8) = imazamethabenz-methyl (Assert ® )
( ) = % efficacy of individual active substances

TABLE 4

| Active substance(s) | g of a.i./ha | ECHCR % control | ZEAMA % damage |
|---|---|---|---|
| A) | 10 | 65 | 0 |
|  | 20 | 75 | 0 |
|  | 40 | 80 | 0 |
|  | 80 | 88 | 0 |
| B13) | 15 | 0 | 0 |
|  | 30 | 73 | 0 |
|  | 60 | 75 | 2 |
| A) + B13) | 10 + 15 | 97 (65 + 0) | 3 |
| B14) | 5 | 15 | 0 |
|  | 10 | 60 | 2 |
|  | 20 | 85 | 3 |
| A) + B14) | 10 + 5 | 80 (65 + 15) | 0 |
|  | 10 + 10 | {70} | 0 |
|  |  | 92 (65 + 60) |  |
|  |  | {86} |  |

ECHCR = *Echinochloa crus galli*
ZEAMA = *Zea mays*
A) = sodium salt of methyl 4-iodo-2-[3-(4-methoxy-6-methyl-1,3,5-triazin-2-yl)ureidosulfonyl]benzoate
B13) = nicosulfuron
B14) = rimsulfuron
( ) = % efficacy of the individual active substances
{ } = expected value using Colby's formula

TABLE 5

| Active substance(s) | g of a.i./ha | LOLMU % control | FALCO % control | TRZAW % damage |
|---|---|---|---|---|
| A) | 2.5 | 68 | 73 | 0 |
|  | 5 | 75 | 85 | 0 |
|  | 10 | 83 | 88 | 0 |
|  | 20 |  | 97 | 10 |
|  | 40 |  | 98 | 15 |
|  | 80 |  | 99 | 18 |
|  | 160 |  | 99 | 28 |
| B17) | 250 |  | 0 | 0 |
|  | 500 |  | 68 |  |
|  | 1000 |  | 75 |  |
| A) + B17) | 10 + 250 |  | 94 (88 + 0) | 0 |
|  | 5 + 500 |  | 98 (85 + 68) | 0 |
|  |  |  | {95} |  |

TABLE 5-continued

| Active substance(s) | g of a.i./ha | LOLMU % control | FALCO | TRZAW % damage |
|---|---|---|---|---|
| B16) | 125 | | 0 | 0 |
| | 250 | | 15 | 0 |
| | 500 | | 55 | 0 |
| | 1000 | | 68 | 0 |
| A) + B16) | 10 + 125 | | 91 (88 + 0) | 0 |
| B20) | 50 | 5 | | 0 |
| | 100 | 10 | | 0 |
| | 200 | 18 | | 0 |
| | 400 | 40 | | 10 |
| A) + B20) | 5 + 50 | 78 (75 + 5) {76} | | 0 |
| | 10 + 100 | 94 (93 + 10) {86} | | 0 |
| B21) | 50 | | 73 | |
| | 100 | | 80 | |
| | 200 | | 95 | |
| A) + B21) | 5 + 100 | | 99 {97} | 0 |
| | 10 + 50 | | 98 {97} | 0 |
| | 10 + 100 | | 100 {98} | 0 |

LOLMU = *Lolium multiflorum*
FALCO = *Fallopia colvolvulus*
TRZAW = *Triticum aestivum*l
A) = sodium salt of methyl 4-iodo-2-[3-(4-methoxy-6-methyl-1,3,5-triazin-2-yl)ureidosulfonyl]benzoate
B17) = MCPA sodium salt
B16) = mecoprop-P
B20) = dicamba
B21) = fluroxypyr (Starane ® )
( ) = % efficacy of the individual active substances
{ } = expected value using Colby's formula

TABLE 6

| Active substance(s) | g of a.i./ha | CENCY % control | SECCW % damage |
|---|---|---|---|
| A) | 5 | 0 | 0 |
| | 10 | 30 | 0 |
| | 15 | 60 | 5 |
| B16) | 600 | 30 | 0 |
| | 2500 | 70 | 0 |
| A) + B16) | 10 + 600 | 100 (30 + 30) | 0 |

CENCY = *Centaurea cyanus*
SECCW = *Secale cereale*
A) = sodium salt of methyl 4-iodo-2-[3-(4-methoxy-6-methyl-1,3,5-triazin-2-yl)ureidosulfonyl]benzoate
B16) = mecoprop-P
( ) = % efficacy of the individual active substances

TABLE 7

| Active substance(s) | g of a.i./ha | GALAP % control | VIOAR | TRZAW % damage |
|---|---|---|---|---|
| A) | 2.5 | 35 | 58 | 0 |
| | 5 | 58 | 75 | 0 |
| | 10 | 60 | 95 | 2 |
| | 20 | 99 | 98 | 10 |
| B22) | 62.5 | 0 | | 0 |
| | 125 | 3 | | 0 |
| | 250 | 10 | | 0 |
| | 500 | 18 | | 0 |
| A) + B22) | 10 + 125 | 68 (60 + 3) | | 0 |
| | 10 + 250 | 85 (60 + 10) | | 0 |
| B25) | 4 | | 3 | 0 |
| | 8 | | 18 | 0 |
| | 15 | | 38 | 0 |
| | 30 | | 62 | 0 |
| A) + B25) | 5 + 15 | | 93 (75 + 38) {85 } | 0 |

TABLE 7-continued

| Active substance(s) | g of a.i./ha | GALAP % control | VIOAR | TRZAW % damage |
|---|---|---|---|---|
| B32) | 13 | 0 | | 0 |
| | 25 | 0 | | 0 |
| | 50 | 5 | | 0 |
| | 100 | 5 | | 0 |
| A) + B32) | 10 + 13 | 98 (60 + 0) | | 0 |

LOLMU = *Lolium multiflorum*
VIOAR = *Viola arvensis*
TRZAW = *Triticum aestivum*
A) = sodium salt of methyl 4-iodo-2-[3-(4-methoxy-6-methyl-1,3,5-triazin-2-yl)ureidosulfonyl]benzoate
B32) = ioxynil
B25) = fluoroglycofen-ethyl (Compete ® )
B32) = diflufenican
( ) = % efficacy of the individual active substances
{ } = expected value using Colby's formula

TABLE 8

| Active substance(s) | g of a.i./ha | ECHCR % control | ZEAMA % damage |
|---|---|---|---|
| A) | 10 | 65 | 0 |
| | 20 | 73 | 0 |
| | 40 | 80 | 0 |
| | 80 | 88 | 0 |
| B36) | 375 | 0 | 0 |
| | 750 | 0 | 0 |
| | 1500 | 3 | 0 |
| | 3000 | 3 | 0 |
| A) + B36) | 10 + 375 | 88 (65 + 0) | 0 |
| | 10 + 750 | 93 (65 + 0) | 0 |

ECHCR = *Echinochloa crus galli*
ZEAMA = *Zea mays*l
A) = sodium salt of methyl 4-iodo-2-[3-(4-methoxy-6-methyl-1,3,5-triazin-2-yl)ureidosulfonyl]benzoate
B36) = atrazine
( ) = % efficacy of the individual active substances

TABLE 9

| Active substance(s) | g of a.i./ha | FALCO % control | CENCY | TRZAW % damage |
|---|---|---|---|---|
| A) | 2.5 | 73 | 30 | 0 |
| | 5 | 85 | 43 | 0 |
| | 10 | 88 | 58 | 2 |
| | 20 | 97 | 78 | 10 |
| | 40 | 98 | | 15 |
| B41) | 1 | 0 | 0 | 0 |
| | 3 | 0 | 0 | 0 |
| | 5 | 0 | 0 | 0 |
| | 10 | 0 | 0 | 0 |
| A) + B41) | 2.5 + 3 | | 50 (30 + 0) | 0 |
| | 5 + 3 | | 75 (43 + 0) | 0 |
| | 10 + 3 | | 78 (58 + 0) | 0 |
| B42) | 5 | 88 | | 0 |
| | 10 | 93 | | 0 |
| | 20 | 95 | | 0 |
| | 40 | 97 | | 0 |
| A) + B42) | 5 + 5 | 100 (85 + 88) {98} | | 0 |

CENCY = *Centaurea cyanus*
FALCO = *Fallopia convolvulus*
TRZAW = Triticum aestivum
A) = sodium salt of methyl 4-iodo-2-[3-(4-methoxy-6-methyl-1,3,5-triazin-2-yl)ureidosulfonyl]benzoate
B41) = metsulfuron-methyl (Gropper ® )
B42) = tribenuron-llmethyl (Pointer ® )
( ) = % efficacy of the individual active substances
{ } = Expected value using Colby's formula

TABLE 10

| Active substance(s) | g of a.i./ha | CENCY % control | SECCW % damage |
|---|---|---|---|
| A) | 5 | 0 | 0 |
|  | 10 | 30 | 0 |
|  | 15 | 60 | 5 |
| B40) | 20 | 25 | 0 |
| A) + B40) | 10 + 20 | 95 (30 + 25) | 0 |

CENCY = *Centaurea cyanus*
SECCW = *Secale cereale*
A) = sodium salt of methyl 4-iodo-2-[3-(4-methoxy-6-methyl-1,3,5-triazin-2-yl)ureidosulfonyl]benzoate
B40) = amidosulfuron
( ) = % efficacy of the individual active substances

TABLE 11

| Active substance(s) | g of a.i./ha | GALAP | AVEFA % control | MERAN |
|---|---|---|---|---|
| A) | 5 | 75 | 60 | 70 |
|  | 10 | 98 | 80 | 94 |
| B49) | 150 | 55 | 60 | 65 |
|  | 300 | 73 | 70 | 78 |
|  | 450 | 85 | 80 | 90 |
| A) + B49) | 5 + 150 | 99 (75 + 55) {89} | 90 (60 + 60) {84} | 98 (70 + 65) {98} |

GALAP = *Gallium aparine*
AVEFA = *Avena fatua*
MERAN = *Mercurialis annua*
A) = sodium salt of methyl 4-iodo-2-[3-(4-methoxy-6-methyl-1,3,5-triazin-2-yl)ureidosulfonyl]benzoate
B49) = glufosinate-ammonium
( ) = % efficacy of the individual active substances
{ } = expected value using Colby's formula The examples demonstrate that certain weeds can only be controlled thoroughly by the individual active substances when these are used at high dosages. When applied at low dosages, the efficacy of the components is, as a rule, only poor and falls far short of what is required under realistic conditions. Good effects against all weed species tested can only be achieved by applying the active substances jointly. The additive efficacy of the individual components was exceeded markedly, i.e. the control level required was achieved by markedly lower rates of application. These effects widen the spectrum of action markedly.

The compatibility with crops, which is assessed in the form of damage, is not adversely affected, i.e. the combinations can be considered fully selective.

Other advantages and use forms of the invention can be seen from the patent claims which follow.

TABLE 12

| Active substance(s) | g of ai/ha | ABUTHE | AMBEL % control | ZEAMA % damage |
|---|---|---|---|---|
| A) | 2.5 | 10 | 88 | 3 |
| B31) | 4.5 | 60 | 0 | 5 |

TABLE 12-continued

| Active substance(s) | g of ai/ha | ABUTHE | AMBEL % control | ZEAMA % damage |
|---|---|---|---|---|
| A) + b52) | 2.5 + 4.5 | 89(60 + 10) | 95(88 + 0) | 7 |

ABUTHE = *Abuthilon theophrastis*
AMBEL = *Ambrosia elatior*
ZEAMA = *Zea mays*
A) = sodium salt of methyl 4-iodo-2-[3-(4-methoxy-6-methyl-1,3,5-triazin-2-yl)ureidosulfonyl]benzoate
B52) = carfentrazone-ethyl:

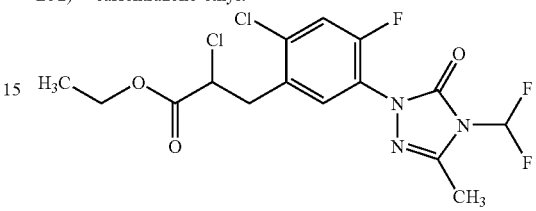

(+) = % efficacy of the individual active substance(s) (additive method)

The invention claimed is:

1. A synergistic herbicidal composition comprising synergistically effective amounts of
A) at least one compound from the group of the substituted phenylsulfonylureas of the formula I and their agriculturally acceptable salts

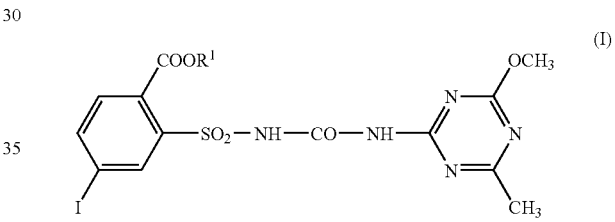

in which
$R^1$ is $(C_1-C_8)$alkyl
and
B) at least one herbicidally active compound from the group of compounds selected from the group consisting of
Ba) one or more herbicides which act selectively against grasses in cereals and/or maize selected from the group consisting of
B8) imazamethabenz and imazamethabenz methyl

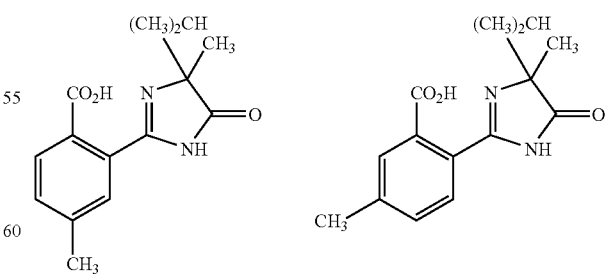

and
Bb) one or more herbicides which act selectively against dicots in cereals and/or maize selected from the group consisting of B16) mecoprop, mecoprop-P

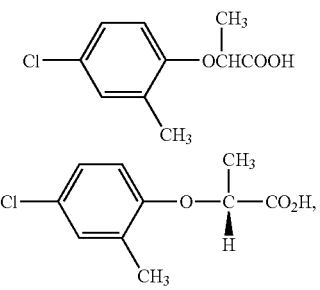

B22) ioxynil

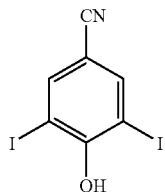

or ioxynil-octanoate or ioxynil-sodium, and
B33) bentazone

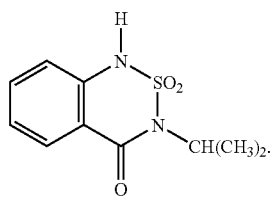

2. The composition as claimed in claim 1, wherein for the compounds of formula (I) or salts thereof, $R_1$ is methyl, ethyl, n-propyl, isopropyl, n-, tert-, 2-butyl or isobutyl, n-pentyl, isopentyl, n-hexyl, isohexyl, 1,3-dimethylbutyl, n-heptyl, 1-methylhexyl or 1,4-dimethylpentyl.

3. The composition as claimed in claim 1, wherein for the compounds of formula (I) or salts thereof, $R_1$ is methyl.

4. The composition of claim 1, wherein the salts of the herbicide of the formula (I) are formed by replacing the hydrogen of the —$SO_2$—NH— group by a cation selected from the group consisting of alkali metals, alkaline earth metals and ammonium.

5. The composition as claimed in claim 1, wherein the group B herbicide is imazamethabenz, imazamethabenz methyl, mecoprop, mecoprop-P, ioxynil, or bentazone.

6. The composition as claimed in claim 1, which comprises 0.1 to 9% by weight of at least one compound of formula I or salts thereof and at least one group B herbicide.

7. The composition as claimed in claim 1, wherein the group B herbicide is imazamethabenz, imamazamethabenz methyl, mecoprop, mecoprop-P, or ioxynil.

8. The composition as claimed in claim 1, wherein the group B herbicide is
B33) bentazone

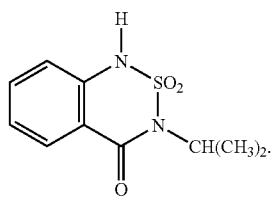

9. A method of controlling undesirable plants, which comprises applying the synergistic herbicidal composition according to claim 1 to said undesirable plants or to an area under cultivation.

10. The method as claimed in claim 1, wherein the rate of application for the compounds of formula (I) or salts thereof is from 0.1 to 100 g of ai./ha and the rate for the group B herbicide is from 1 to 5000 g of a.i./ha.

11. The method as claimed in claim 1, wherein the rate of application for the compound of formula (I) or salts thereof is from 2 to 40 g of a.i./ha.

12. The method according to claim 1, wherein said at least one compound of formula I or salts thereof and said at least one herbicide of group B are applied in a weight ratio of 1:2500 to 20:1, either simultaneously or at separate points in time.

13. The method according to claim 1, wherein the synergistic herbicidal composition is employed in transgenic crops, or in cereals, maize, rice, sugar cane, plantation crops, grasslands or pastures.

14. The method according to claim 1, wherein the synergistic herbicidal composition is for the selection control of undesirable plants.

* * * * *